(12) United States Patent
Wichem et al.

(10) Patent No.: US 10,206,561 B2
(45) Date of Patent: Feb. 19, 2019

(54) VIDEOSTROBOSCOPY OF VOCAL CORDS WITH CMOS SENSORS

(71) Applicant: Depuy Synthes Products, Inc., Raynham, MA (US)

(72) Inventors: Donald M. Wichem, South Ogden, UT (US); Joshua D. Talbert, Cottonwood Heights, UT (US); Laurent Blanquart, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 167 days.

(21) Appl. No.: 14/194,065

(22) Filed: Feb. 28, 2014

(65) Prior Publication Data

US 2014/0316196 A1    Oct. 23, 2014

Related U.S. Application Data

(60) Provisional application No. 61/770,518, filed on Feb. 28, 2013.

(51) Int. Cl.
| | |
|---|---|
| *A61B 1/06* | (2006.01) |
| *A61B 1/05* | (2006.01) |
| *A61B 1/00* | (2006.01) |
| *A61B 1/267* | (2006.01) |
| *A61B 1/04* | (2006.01) |

(52) U.S. Cl.
CPC ........ *A61B 1/0676* (2013.01); *A61B 1/00006* (2013.01); *A61B 1/00009* (2013.01); *A61B 1/042* (2013.01); *A61B 1/05* (2013.01); *A61B 1/0661* (2013.01); *A61B 1/0684* (2013.01); *A61B 1/2673* (2013.01)

(58) Field of Classification Search
CPC .... H04N 5/2355; H04N 5/3532; H04N 5/357; H04N 5/3595; H04N 5/3597
USPC ......................................... 348/370, 371, 579
See application file for complete search history.

(56) References Cited

U.S. PATENT DOCUMENTS

| | | | | |
|---|---|---|---|---|
| 4,222,394 | A * | 9/1980 | Nagashima | A61B 1/2673 600/586 |
| 4,232,685 | A * | 11/1980 | Nagashima | A61B 1/04 396/16 |
| 4,273,959 | A * | 6/1981 | Tuda | H05B 41/34 704/276 |
| 4,433,675 | A | 2/1984 | Konoshima | |
| 4,535,758 | A * | 8/1985 | Longacre, Jr. | H04N 5/2352 348/230.1 |
| 4,567,524 | A * | 1/1986 | Levine | H04N 5/3595 257/229 |

(Continued)

FOREIGN PATENT DOCUMENTS

WO    WO 2011076159 A2    6/2011

*Primary Examiner* — Timothy J Neal
*Assistant Examiner* — Jae Woo
(74) *Attorney, Agent, or Firm* — Terrence J. Edwards; TechLaw Ventures, PLLC

(57) ABSTRACT

The disclosure relates and extends to a light source having a strobing or pulsing sequence suitable for use with a CMOS sensor that does not require, have, or use a global shutter. Instead, the CMOS sensor synchronizes the strobing input with the blanking portion of the sensor readout pattern and disables the strobing during sensor readout, or when the strobing would otherwise leave artifacts in the image. The CMOS sensor freezes its readout during the strobing.

14 Claims, 16 Drawing Sheets

(56) References Cited

U.S. PATENT DOCUMENTS

| | | | |
|---|---|---|---|
| 4,594,612 A * | 6/1986 | Levine | H04N 5/3595 348/249 |
| 4,616,636 A * | 10/1986 | Nagashima | H05B 41/34 315/241 S |
| 4,635,123 A * | 1/1987 | Masunaga | H04N 5/335 348/296 |
| 4,661,854 A * | 4/1987 | Savoye | H04N 5/3595 348/248 |
| 4,782,386 A * | 11/1988 | Ams | A61B 1/042 348/371 |
| 4,866,526 A * | 9/1989 | Ams | A61B 1/05 348/364 |
| 4,972,267 A * | 11/1990 | Kaneko | H04N 5/3595 348/243 |
| 5,025,319 A * | 6/1991 | Mutoh | H04N 5/3595 348/248 |
| 5,031,048 A * | 7/1991 | Naruto | H04N 5/2351 348/296 |
| 5,187,572 A | 2/1993 | Nakamura et al. | |
| 5,196,938 A | 3/1993 | Blessinger | |
| 5,241,170 A | 8/1993 | Field, Jr. et al. | |
| 5,461,425 A | 10/1995 | Fowler et al. | |
| 5,471,515 A | 11/1995 | Fossum et al. | |
| 5,665,959 A | 9/1997 | Fossum et al. | |
| 5,748,234 A | 5/1998 | Lippincott | |
| 5,784,099 A | 7/1998 | Lippincott | |
| 5,841,126 A | 11/1998 | Fossum et al. | |
| 5,887,049 A | 3/1999 | Fossum | |
| 5,929,901 A | 7/1999 | Adair et al. | |
| 5,949,483 A | 9/1999 | Fossum et al. | |
| 5,990,506 A | 11/1999 | Fossum et al. | |
| 6,005,619 A | 12/1999 | Fossum | |
| 6,021,172 A | 2/2000 | Fossum et al. | |
| 6,027,955 A | 2/2000 | Lee et al. | |
| 6,028,330 A | 2/2000 | Lee et al. | |
| 6,088,058 A * | 7/2000 | Mead | H04N 5/353 257/291 |
| 6,096,573 A | 8/2000 | Chen | |
| 6,101,232 A | 8/2000 | Fossum et al. | |
| 6,118,142 A | 9/2000 | Chen et al. | |
| 6,166,367 A | 12/2000 | Cho | |
| 6,166,768 A | 12/2000 | Fossum et al. | |
| 6,180,969 B1 | 1/2001 | Yang et al. | |
| 6,181,300 B1 * | 1/2001 | Poon | G09G 5/12 345/213 |
| 6,184,055 B1 | 2/2001 | Yang et al. | |
| 6,192,074 B1 * | 2/2001 | Birks | H04N 5/04 348/E5.009 |
| 6,194,260 B1 | 2/2001 | Chien et al. | |
| 6,198,087 B1 | 3/2001 | Boon | |
| 6,207,984 B1 | 3/2001 | Chang | |
| 6,222,175 B1 | 4/2001 | Krymski | |
| 62,394,546 | 5/2001 | Berezin et al. | |
| 6,242,277 B1 | 6/2001 | Lin et al. | |
| 6,272,269 B1 | 8/2001 | Naum | |
| 6,303,421 B1 | 10/2001 | Chang | |
| 6,331,156 B1 | 12/2001 | Haefele et al. | |
| 6,333,205 B1 | 12/2001 | Rhodes | |
| 6,388,243 B1 | 5/2002 | Berezin et al. | |
| 6,400,824 B1 | 6/2002 | Mansoorian et al. | |
| 6,410,377 B1 | 6/2002 | Hwang et al. | |
| 6,441,482 B1 | 8/2002 | Foster | |
| 6,456,326 B2 | 9/2002 | Fossum et al. | |
| 6,485,414 B1 | 11/2002 | Neuberger | |
| 6,512,280 B2 | 1/2003 | Chen et al. | |
| 6,515,321 B1 | 2/2003 | Jwo | |
| 6,515,701 B2 * | 2/2003 | Clark | H04N 5/3454 348/308 |
| 6,549,235 B1 | 4/2003 | Fossum et al. | |
| 6,555,842 B1 | 4/2003 | Fossum et al. | |
| 6,570,617 B2 | 5/2003 | Fossum et al. | |
| 6,606,122 B1 | 8/2003 | Shaw et al. | |
| 6,610,557 B2 | 8/2003 | Lee et al. | |
| 6,627,474 B2 | 9/2003 | Barna et al. | |
| 6,631,230 B1 | 10/2003 | Campbell | |
| 6,665,013 B1 | 12/2003 | Fossum et al. | |
| 6,690,466 B2 | 2/2004 | Miller et al. | |
| 6,692,431 B2 | 2/2004 | Kazakevich | |
| 6,704,049 B1 | 3/2004 | Fossum | |
| 6,730,900 B2 | 5/2004 | Hsish et al. | |
| 6,734,893 B1 | 5/2004 | Hess et al. | |
| 6,740,870 B1 | 5/2004 | Doudoumopoulos | |
| 6,744,068 B2 | 6/2004 | Fossum et al. | |
| 6,838,653 B2 | 1/2005 | Campbell et al. | |
| 6,838,716 B2 | 1/2005 | Asada et al. | |
| 6,847,399 B1 | 1/2005 | Ang | |
| 6,873,363 B1 | 3/2005 | Barna et al. | |
| 6,879,340 B1 | 4/2005 | Chevallier | |
| 6,897,082 B2 | 5/2005 | Rhodes et al. | |
| 6,899,675 B2 | 5/2005 | Cline et al. | |
| 6,906,745 B1 | 6/2005 | Fossum et al. | |
| 6,921,920 B2 | 7/2005 | Kazakevich | |
| 6,933,974 B2 | 8/2005 | Lee | |
| 6,961,461 B2 | 11/2005 | MacKinnon et al. | |
| 6,999,118 B2 | 2/2006 | Suzuki | |
| 7,002,231 B2 | 2/2006 | Rhodes et al. | |
| 7,009,646 B1 | 3/2006 | Fossum et al. | |
| 7,009,648 B2 | 3/2006 | Lauxtermann et al. | |
| 7,037,259 B2 | 5/2006 | Hakamata et al. | |
| 7,050,094 B2 | 5/2006 | Krymski | |
| 7,079,178 B2 | 7/2006 | Hynecek | |
| 7,105,371 B2 | 9/2006 | Fossum et al. | |
| 7,106,367 B2 | 9/2006 | Sarwari | |
| 7,129,108 B2 | 10/2006 | Jang | |
| 7,189,226 B2 | 3/2007 | Auld et al. | |
| 7,202,899 B2 | 4/2007 | Lin et al. | |
| 7,208,983 B2 | 4/2007 | Imaizumi et al. | |
| 7,217,967 B2 | 5/2007 | Han | |
| 7,232,712 B2 | 5/2007 | Han | |
| 7,244,920 B2 | 7/2007 | Kim et al. | |
| 7,250,594 B2 | 7/2007 | Lin et al. | |
| 7,258,663 B2 | 8/2007 | Doguchi et al. | |
| 7,280,139 B2 | 10/2007 | Pahr et al. | |
| 7,338,832 B2 | 3/2008 | Park et al. | |
| 7,354,841 B2 | 4/2008 | Jeon | |
| 7,368,771 B2 | 5/2008 | Roh et al. | |
| 7,369,166 B2 | 5/2008 | Fossum et al. | |
| 7,397,076 B2 | 7/2008 | Jang | |
| 7,488,637 B2 | 2/2009 | Kim | |
| 7,511,257 B2 | 3/2009 | Lee et al. | |
| 7,522,341 B2 | 4/2009 | Mouli | |
| 7,525,168 B2 | 4/2009 | Hsieh | |
| 7,532,760 B2 | 5/2009 | Kaplinsky et al. | |
| 7,534,645 B2 | 5/2009 | Choi | |
| 7,540,645 B2 | 6/2009 | Kazakevich | |
| 7,544,163 B2 | 6/2009 | MacKinnon et al. | |
| 7,545,434 B2 | 6/2009 | Bean et al. | |
| 7,564,935 B2 | 7/2009 | Suzuki | |
| 7,567,291 B2 | 7/2009 | Rechtel et al. | |
| 7,573,516 B2 | 8/2009 | Krymski et al. | |
| 7,573,519 B2 | 8/2009 | Phan et al. | |
| 7,589,349 B2 | 9/2009 | Hong | |
| 7,595,210 B2 | 9/2009 | Shim | |
| 7,605,016 B2 | 10/2009 | Min | |
| 7,608,874 B2 | 10/2009 | Lee et al. | |
| 7,612,318 B2 | 11/2009 | Jeon | |
| 7,615,808 B2 | 11/2009 | Pain et al. | |
| 7,615,838 B2 | 11/2009 | Kim | |
| 7,630,008 B2 | 12/2009 | Sarwari | |
| 7,646,407 B2 | 1/2010 | Fossum et al. | |
| 7,663,115 B2 | 2/2010 | Korthout et al. | |
| 7,667,740 B2 * | 2/2010 | Hofer | H04N 5/235 348/226.1 |
| 7,749,799 B2 | 7/2010 | Pain | |
| 7,794,394 B2 | 9/2010 | Frangioni | |
| 7,830,434 B2 | 11/2010 | Li et al. | |
| 7,901,974 B2 | 3/2011 | Venezia et al. | |
| 7,916,193 B2 | 3/2011 | Fossum | |
| 7,923,763 B2 | 4/2011 | Lauxtermann | |
| 7,936,394 B2 | 5/2011 | Wu | |
| 7,952,096 B2 | 5/2011 | Rhodes | |
| 7,973,342 B2 | 7/2011 | Jeon | |
| 7,995,123 B2 | 8/2011 | Lee et al. | |

(56) References Cited

U.S. PATENT DOCUMENTS

| | | |
|---|---|---|
| 8,040,394 B2 | 10/2011 | Fossum et al. |
| 8,054,339 B2 | 11/2011 | Fossum et al. |
| 8,089,542 B2 | 1/2012 | Chevallier |
| 8,101,903 B2 | 1/2012 | Mokhnatyuk |
| 8,144,226 B2 | 3/2012 | Shah et al. |
| 8,154,055 B2 | 4/2012 | Ha |
| 8,384,814 B2 | 2/2013 | Chevallier |
| 8,405,748 B2 | 3/2013 | Mao et al. |
| 8,471,938 B2 | 6/2013 | Altice, Jr. et al. |
| 8,476,575 B2 | 7/2013 | Mokhnatyuk |
| 8,493,474 B2 | 7/2013 | Richardson |
| 8,537,241 B2 | 9/2013 | Ayers et al. |
| 8,610,808 B2 | 12/2013 | Prescher et al. |
| 8,614,754 B2 | 12/2013 | Fossum |
| 8,625,016 B2 | 1/2014 | Fossum et al. |
| 8,629,023 B2 | 1/2014 | Lee |
| 8,648,287 B1 | 2/2014 | Fossum |
| 8,733,660 B2 | 5/2014 | Wang et al. |
| 8,736,007 B2 | 5/2014 | Wu et al. |
| 8,754,358 B2 | 6/2014 | Chou et al. |
| 8,797,434 B2 | 8/2014 | Lee et al. |
| 8,823,846 B2 * | 9/2014 | Blanquart ............ H04N 5/3535 348/294 |
| 8,896,730 B2 | 11/2014 | Fossum |
| 8,988,598 B2 * | 3/2015 | Ovsiannikov ........ H04N 5/2354 348/370 |
| 2001/0030744 A1 | 10/2001 | Chang |
| 2003/0016189 A1 * | 1/2003 | Abe .................. G09G 3/20 345/55 |
| 2003/0139666 A1 * | 7/2003 | Klemm ............... A61B 1/2673 600/410 |
| 2004/0095464 A1 * | 5/2004 | Miyagi ............... A61B 1/2673 348/65 |
| 2005/0219376 A1 | 10/2005 | Wittenberg et al. |
| 2005/0234302 A1 | 10/2005 | MacKinnon et al. |
| 2005/0253940 A1 * | 11/2005 | Chiba ............... H04N 5/23245 348/247 |
| 2006/0069314 A1 | 3/2006 | Farr |
| 2006/0157760 A1 * | 7/2006 | Hayashi .................. G03B 7/00 257/293 |
| 2007/0040927 A1 * | 2/2007 | Ishigami ............... H04N 5/235 348/348 |
| 2008/0018769 A1 * | 1/2008 | Hatano .................. H04N 5/357 348/312 |
| 2008/0045800 A2 | 2/2008 | Farr |
| 2008/0122969 A1 * | 5/2008 | Alakarhu ............. G03B 43/02 348/362 |
| 2008/0180547 A1 * | 7/2008 | Hirose .................. H04N 5/243 348/229.1 |
| 2008/0252768 A1 * | 10/2008 | Suzuki ................ H04N 5/2254 348/312 |
| 2008/0309810 A1 * | 12/2008 | Smith ................. H04N 5/235 348/319 |
| 2009/0012361 A1 | 1/2009 | MacKinnon et al. |
| 2009/0256850 A1 * | 10/2009 | Yang .................... G09G 5/399 345/536 |
| 2009/0292168 A1 | 11/2009 | Farr |
| 2010/0045502 A1 * | 2/2010 | Ishibashi .................. G09G 3/02 341/145 |
| 2010/0045830 A1 * | 2/2010 | Yuyama ............... H04N 5/3595 348/249 |
| 2010/0049048 A1 * | 2/2010 | Miyachi ................... A61B 8/08 600/443 |
| 2010/0066897 A1 * | 3/2010 | Miyanari ........... H04N 5/23209 348/362 |
| 2010/0073494 A1 * | 3/2010 | Hirose ............... H04N 5/23248 348/208.4 |
| 2010/0123775 A1 | 5/2010 | Shibasaki |
| 2010/0134608 A1 | 6/2010 | Shibasaki |
| 2010/0149393 A1 * | 6/2010 | Zarnowski ............. H04N 9/045 348/302 |
| 2010/0194935 A1 * | 8/2010 | Okado ................. H04N 5/3595 348/243 |
| 2010/0237837 A1 * | 9/2010 | Wang ................ H02M 3/33507 323/234 |
| 2010/0283880 A1 * | 11/2010 | Kobayashi ........... H04N 5/3595 348/300 |
| 2010/0324374 A1 * | 12/2010 | Kim ..................... A61B 1/2673 600/199 |
| 2010/0329657 A1 * | 12/2010 | Hosoi .................... G03B 15/16 396/169 |
| 2011/0001859 A1 * | 1/2011 | Matsuura ............. H04N 5/2354 348/296 |
| 2011/0066382 A1 * | 3/2011 | Adams ................. G01N 15/147 702/19 |
| 2011/0141318 A1 * | 6/2011 | Lee ................... H01L 27/14618 348/240.2 |
| 2011/0181840 A1 | 7/2011 | Cobb |
| 2011/0237882 A1 | 9/2011 | Saito |
| 2011/0237884 A1 | 9/2011 | Saito |
| 2012/0004508 A1 | 1/2012 | McDowall et al. |
| 2012/0029364 A1 * | 2/2012 | Greenhut ............. A61N 1/3987 600/485 |
| 2012/0033118 A1 | 2/2012 | Lee et al. |
| 2012/0041267 A1 | 2/2012 | Benning et al. |
| 2012/0078052 A1 | 3/2012 | Cheng |
| 2012/0300105 A1 * | 11/2012 | Deever ................ H04N 5/3456 348/302 |
| 2014/0078277 A1 * | 3/2014 | Dai ..................... A61B 1/00004 348/68 |
| 2014/0104466 A1 | 5/2014 | Fossum |
| 2014/0175591 A1 | 6/2014 | Tian et al. |
| 2014/0217268 A1 | 8/2014 | Schleipen et al. |
| 2015/0002708 A1 * | 1/2015 | Marumoto ............. H04N 9/045 348/280 |
| 2015/0271886 A1 * | 9/2015 | Upton ................ H05B 33/0845 315/209 R |
| 2015/0296155 A1 * | 10/2015 | Tanaka ............... H04N 5/3595 348/249 |

\* cited by examiner

VIDEOSTROBOSCOPY OF VOCAL CORDS WITH CMOS SENSORS

CROSS-REFERENCE TO RELATED APPLICATIONS

This application claims the benefit of U.S. Provisional Application No. 61/770,518, filed Feb. 28, 2013, which is hereby incorporated by reference herein in its entirety, including but not limited to those portions that specifically appear hereinafter, the incorporation by reference being made with the following exception: In the event that any portion of the above-referenced provisional application is inconsistent with this application, this application supersedes said above-referenced provisional application.

STATEMENT REGARDING FEDERALLY SPONSORED RESEARCH OR DEVELOPMENT

Not Applicable.

BACKGROUND

Advances in technology have provided advances in imaging capabilities for medical use. One area that has enjoyed some of the most beneficial advances is that of endoscopy, including videostroboscopy, surgical procedures because of the advances in the components that make up the endoscope.

A fairly common procedure used in diagnosing vocal chord issues, such as the structure of a patient's larynx, is videostroboscopy of the vocal chords. The procedure is performed using either a rigid or flexible endoscope, a light source capable of being strobed and a microphone. Light sources might include but are not limited to Xenon, LED, Laser and Halogen. During the procedure, the imaging end of the endoscope is brought into view of the patient's vocal chords and then the patient is asked to speak, repeat key phrases, or sing. The microphone is used to pick up the frequency of the patient's voice and the light source is strobed at a similar frequency which provides a slow-motion view of the vocal chords. The physician then uses the slow motion view to diagnose any vocal chord issues.

Traditionally, CCD (charge-coupled device) type endoscopes are required for any application that requires strobing. The basic approach is to continually strobe the light source at the desired frequency. Because CCD sensors use global shuttering, the strobing may continue without any issue in video quality. However, CCD sensors are substantially more expensive than Complementary Metal Oxide Semiconductor (CMOS) sensors and are known to be inferior to CMOS image sensors in key areas.

In regards to sensor technology, CMOS image sensors have largely displaced conventional CCD imagers in modern camera applications such as endoscopy, owing to their greater ease of integration and operation, superior or comparable image quality, greater versatility and lower cost.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

The disclosure relates to and describes a strobing sequence suitable for use with a CMOS sensor that does not require, have, or use a global shutter. Instead, the CMOS sensor synchronizes the strobing input with the blanking portion of the sensor readout pattern and disables the strobing during sensor readout, or when the strobing would otherwise leave artifacts in the image. As discussed and illustrated herein, the disclosure provides devices, systems and methods that can do this in an efficient and elegant manner.

Figure 1A:
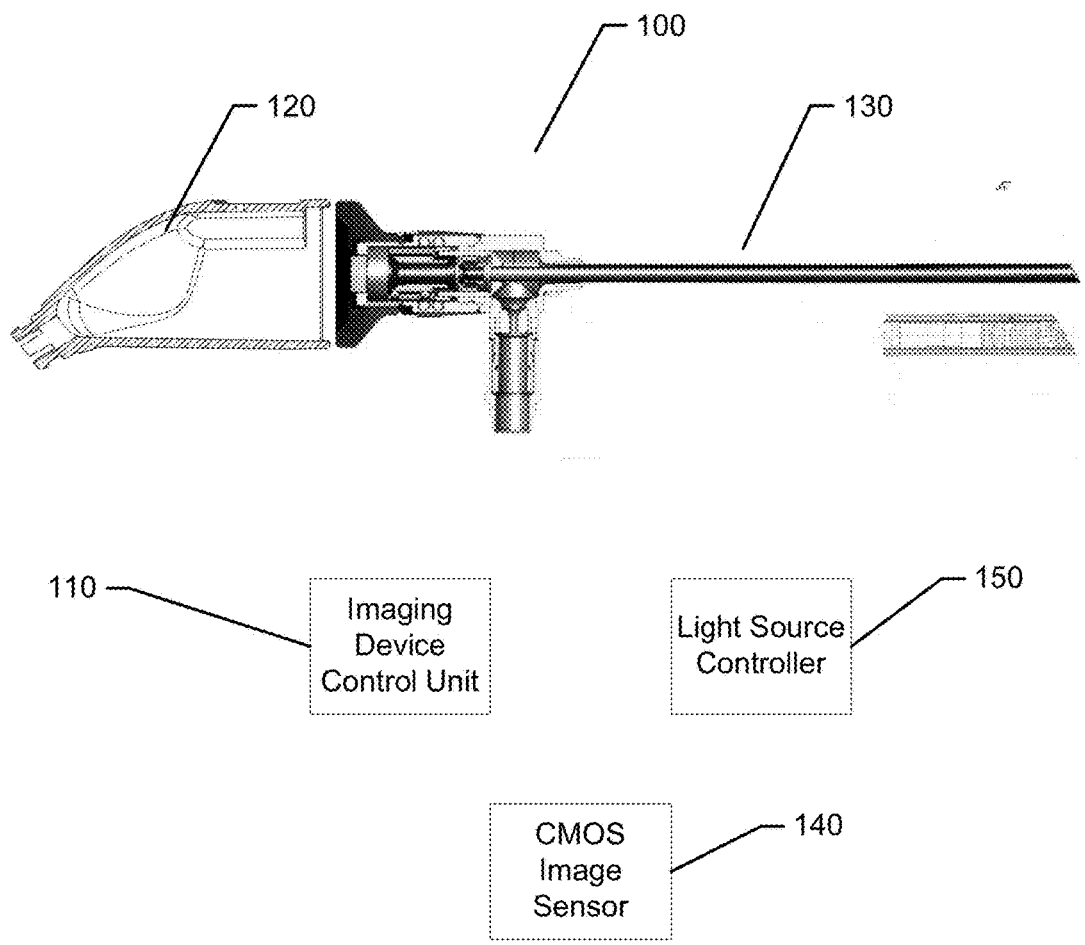
FIG. 1A illustrates an endoscopic system for use in videostroboscopy according to one implementation.

Referring now to the figures, it will be appreciated that the disclosure relates to an endoscopic system 100 as illustrated in FIG. 1A. The endoscopic system 100 may comprise a control unit 110, a camera handpiece 120, an endoscopic device 130, a CMOS image sensor 140, and a light source 150, which may be a strobing light source, a laser light source, an LED light source, or other light source that may be pulsed. It will be appreciated that in one implementation the control unit 110 may be located remotely from an image sensor 140 (discussed more fully herein). In an implementation, the control unit 110 may be located in the handpiece 120. In an implementation the control unit 110 may be located remotely from the image sensor 140 and the handpiece 120 and may be housed at a base unit without departing from the scope of the disclosure.

It is to be understood that the image sensor 140 of the disclosure is a CMOS sensor. The disclosure does not use a CCD sensor and does not utilize a global shutter, which is the current industry standard. Instead, CMOS sensors use electronic shuttering, also referred to as a rolling shutter, to control the amount of light that interacts with the sensor as described more fully herein.

Figure 1B:
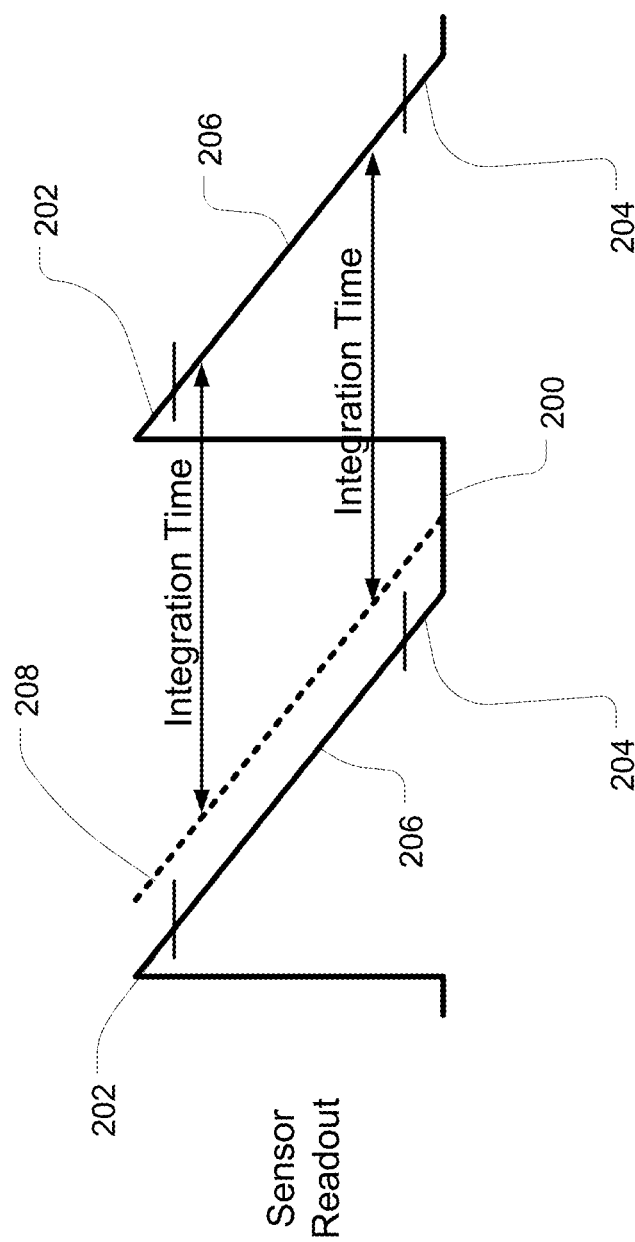
FIG. 1B illustrates a typical readout sequence for a CMOS sensor using an electronic shutter to control the amount of light that hits the sensor according to one implementation.

Referring now to FIG. 1B, a typical readout sequence for a CMOS sensor using an electronic shutter to control the amount of light that hits, or interacts with, the sensor is shown. It will be understood that the sensor readout is illustrated in the figure as being in the y-axis, whereas the integration time is illustrated along the x-axis of the figure. CMOS sensors 140 may comprise an optical black area on or around the front and back rows of the sensor. The optical black areas for the front rows are identified in the figures as 202 and the optical black areas for the back rows are identified in the figures as 204. The readout of the sensor is identified as 206. In FIG. 1B, the electronic shutter or rolling shutter is illustrated by the dashed line labeled 208.

Figure 2:
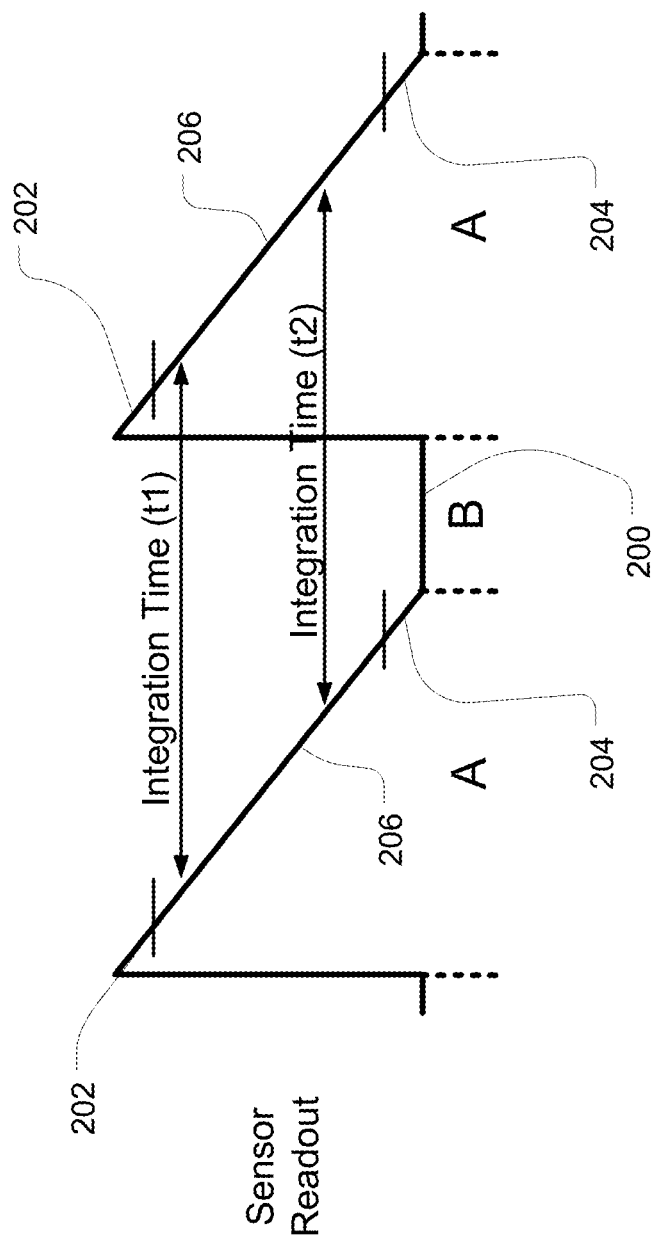
FIG. 2 illustrates a readout sequence for a CMOS sensor where an electronic shutter is switched off and light is integrated from readout to readout according to one implementation.

Referring now to FIG. 2, if the electronic shutter is switched off (for example, there is no extra reset pointer within the frame), the light is integrated from readout to readout as shown. This is known as full frame integration operation. The pixels are read out during time A, B in the blanking area 200. In this configuration, pixels in CMOS sensors are always collecting light. As illustrated, t1 is the time the pixel represented by the line t1 is collecting light, t2 is the time the pixel represented by the line t2 is collecting light.

If the light level changes, for example, the light level increases, during readout of a frame of data, the pixels later in the frame array gather more light than those at the beginning of the frame. Alternatively, if the light level decreases during readout of a frame, the pixels later in the frame gather less light than those at the beginning of the frame.

Figure 3:
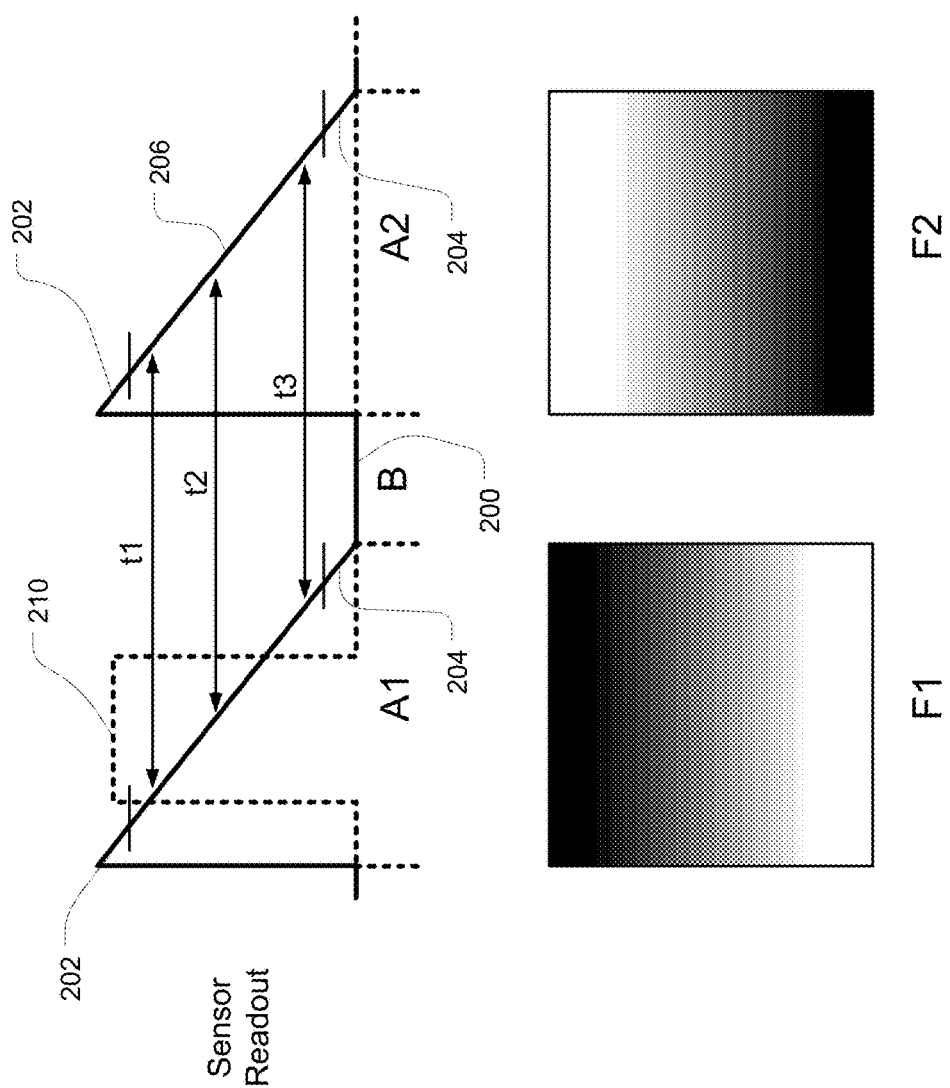
FIG. 3 illustrates a strobe or pulse of light occurring during a read out period, illustrated as A1, according to one implementation.

Referring now to FIG. 3, a light strobe or pulse 210 may occur during the read out period A1. It will be appreciated that the typical range for light strobing is 60 Hz to 1000 Hz, but any other frequency outside this range falls within the scope of this disclosure. The boxes labeled F1 and F2 represent the image resulting from that strobe or pulse 210 of light. Intuitively, one would expect to see a lighter colored bar in the image F1 related to A1 and expect F2 to contain no light information at all. Instead, because the pixels are continually capturing light information, F1 is black until the pulse 210 begins. As the pulse 210 persists in the frame, there is a gradient of light collected between A1.t1 and A1.t2. This gradient continues until the pulse 210 finishes, after which every pixel read out contains the same amount of light information. At A2.t1, the pixels have collected part of the pulse information from the previous frame and so a second gradient is seen in the image. This phenomenon creates flickering or rolling noise on the image. This occurs when the CMOS sensor is exposed to pulsing or strobing light.

To mitigate this and other issues, the disclosure has implemented devices, systems and methods to ensure that any pulse of light occurs during the blanking portion of the read out sequence (identified as 200 or B). In one implementation of the disclosure, the readout sequence is suspended during strobing. In one implementation of the disclosure, the light deficit or light excess of each line is mapped and a specific digital gain per row of pixels is applied.

Figure 4:
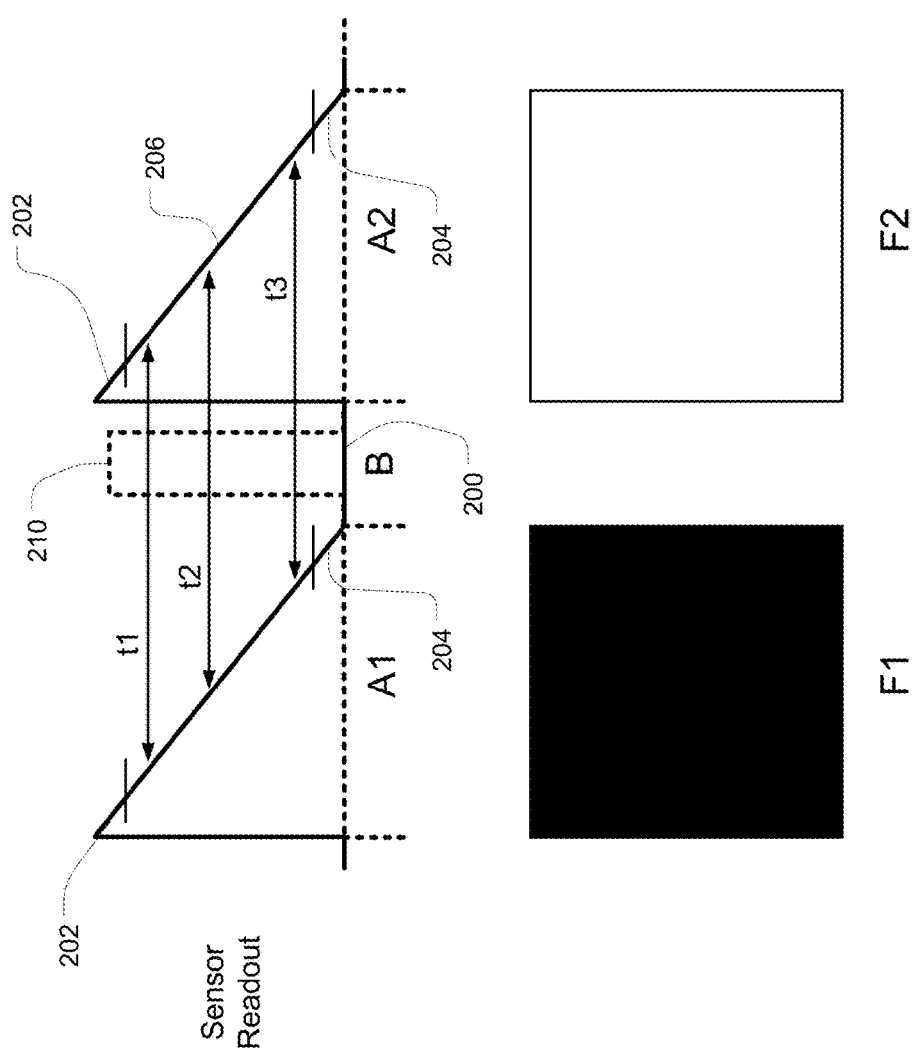
FIG. 4 illustrates a situation in which a frame, represented by read out sequence A1, that will be completely black because it has collected no light information, and the read out sequence represented by A2 will have every pixel exposed by the same amount of light according to one implementation.

Referring now to FIG. 4, where pulsing light during the blanking portion of the read out sequence is illustrated. As illustrated, the frame F1 represented by the read out sequence A1 will be completely black, having collected no light information, and the read out sequence represented by A2 will have every pixel exposed by the same amount of light and will result in the frame F2. As illustrated, B.t1, B.t2 and B.t3 have all been exposed to the same amount of light, which results in the frame F2.

Figure 5:
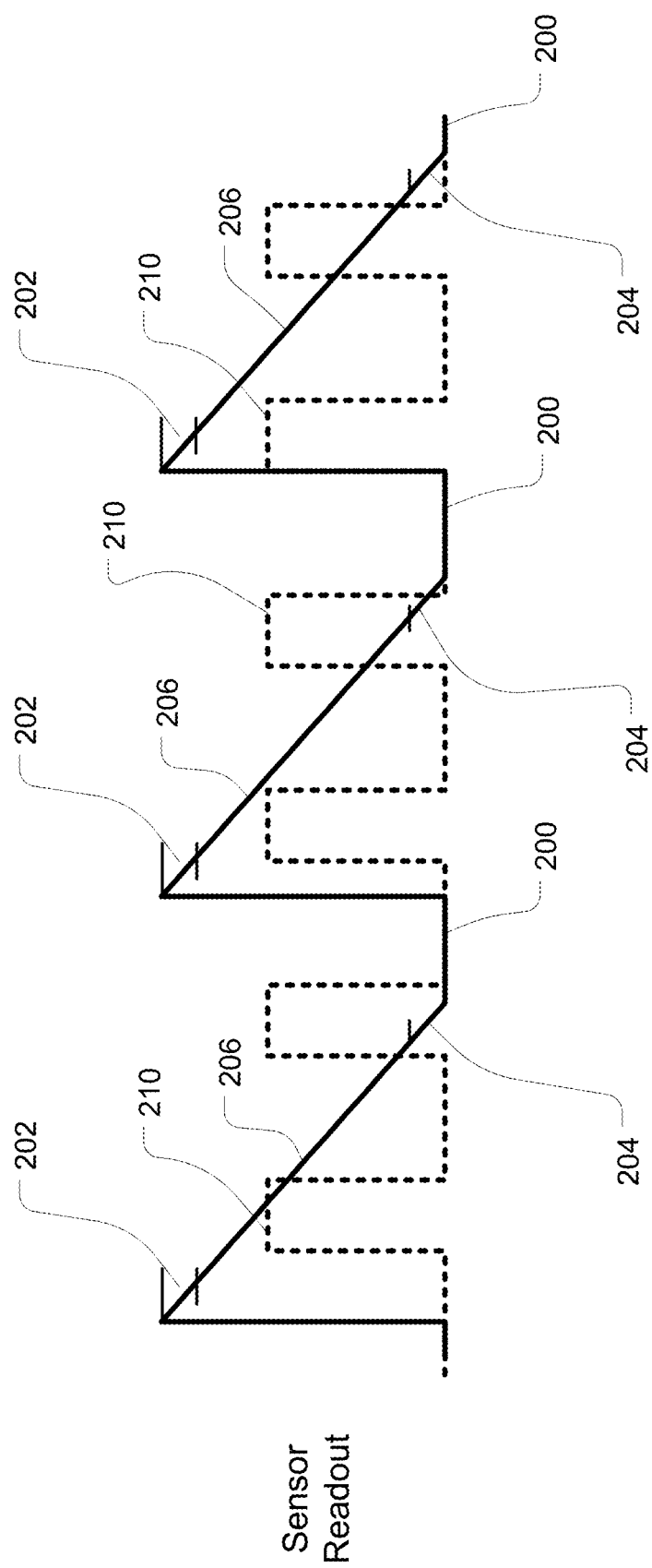
FIG. 5 illustrates an example of a typical sensor sequence with a strobing light source signal superimposed over the sensor sequence according to one implementation.
Figure 6:
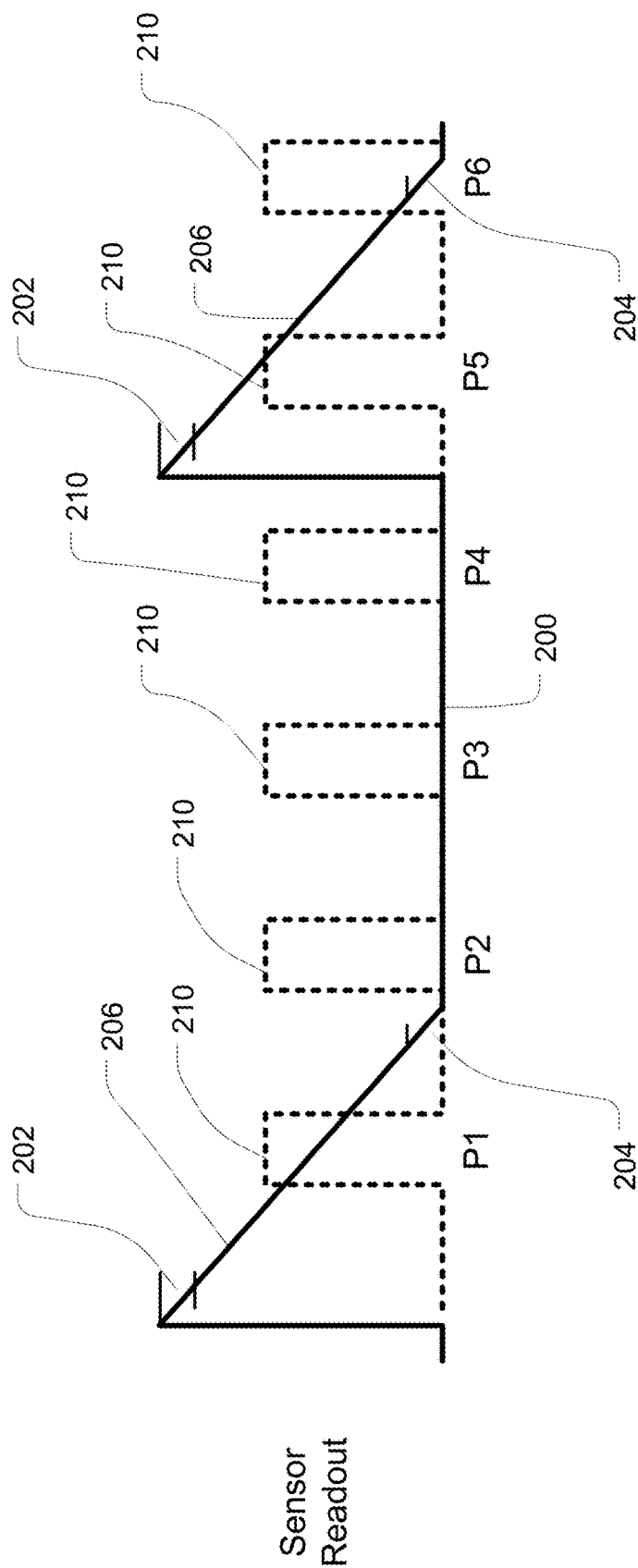
FIG. 6 illustrates extending the blanking portion of a sensor sequence and shortening the pixel read out portion in relation to suppressing pulses of light according to one implementation.

To mitigate the flickering or rolling noise on the image, when the CMOS sensor is exposed to pulsing or strobing light, the CMOS sensor 140 may be strobed or pulsed during its blanking period 200. An example of a typical sensor sequence with a strobing light source signal superimposed over it is depicted in FIG. 5. As illustrated, many of the strobes or pulses 210 occur during the readout portion 206 of the sequence, not during the blanking period 200. Most sensor communication sequences have large readout periods 206 and small blanking periods 200. The disclosure may extend the blanking portion 200 and shorten the pixel read out portion 206 as illustrated and represented by the image in FIG. 6. Note that there is a tradeoff between either running the readout 206 at a higher data rate or sacrificing the number of pixels read out. With the blanking period 200 extended as shown in FIG. 6, it can be seen that full pulses 210 are now present during the blanking period 200.

The next step is to suppress the pulses during the pixel read out portion of the sequence. In FIG. 6, light pulses 210 at P1, P5 and P6 must be suppressed in order to prevent rolling noise or flickering in the image. It should be noted that optical black front 202 and back rows 204 readout can be considered as blanking time 200 as the black pixels will not integrate light. Therefore, a pulse 210 starting right after the start of the optical black back row 204 readout or ending right before the end of optical black front row 202 readout can be considered as a good pulse 210 and should not be rejected.

After suppression of pulses 210 during the pixel readout portion 206, the next step is to ensure that the same number of pulses 210 is captured during each blanking period 200. For example, if two pulses 210 are captured during one blanking period 200 and then one pulse during the next period blanking period 200 the image will still flicker because successive frames have differing light levels due to different number of pulses 210 received during each blanking period 200.

Figure 7:
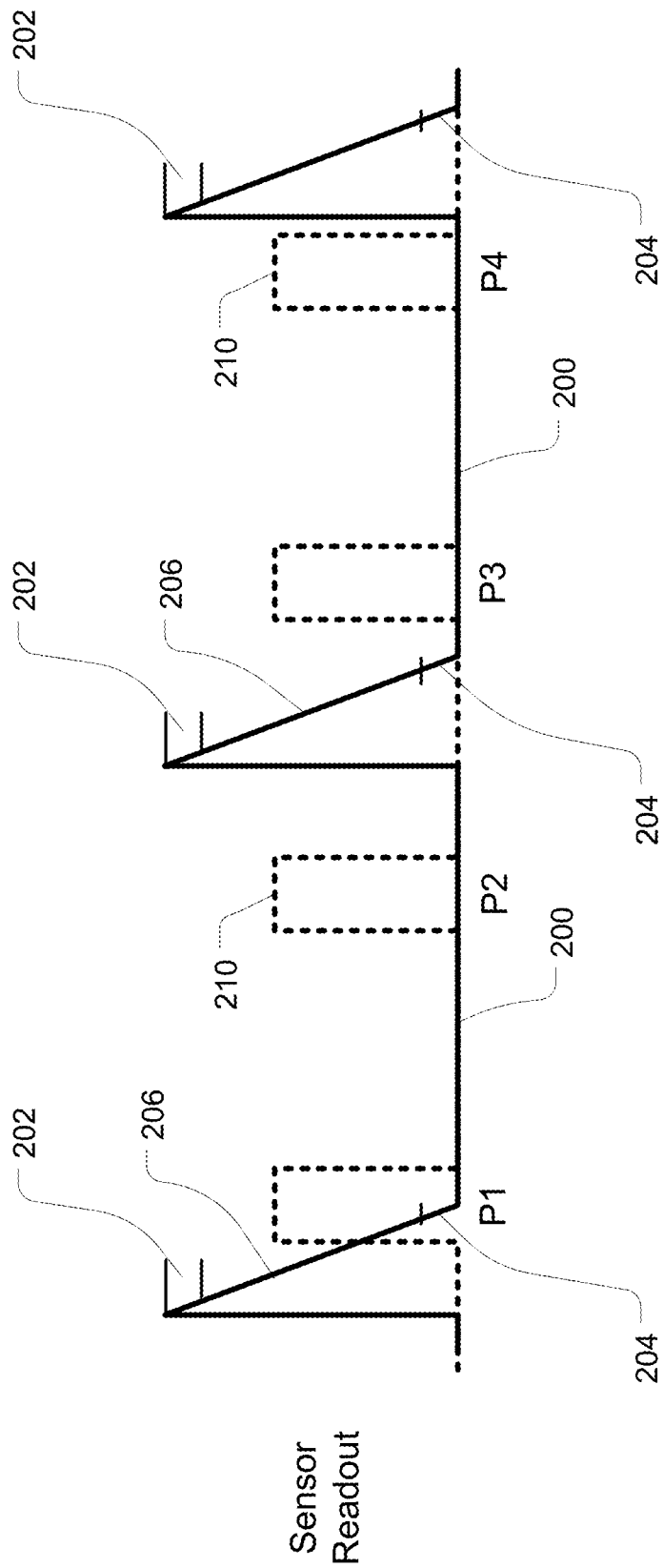
FIG. 7 illustrates the concept of suppressing pulses of light according to one implementation.

Referring now to FIG. 7, in the illustrated figure strobe or pulse 210 at P1 is suppressed because it occurs during the pixel portion of the readout 206. Strobes or pulses 210 at P2, P3 and P4 are not suppressed because they occur during a blanking period 200. However, now the first blanking period 200 has one pulse 210 at P2 and the second blanking period 200 has two pulses 210 at P3 and P4. One of the pulses 210 at P3 or P4 must also be suppressed in order to maintain consistent light exposure.

The final situation or case occurs when a single pulse 210 straddles the pixel readout period 206 and the blanking period 200 of the sequence. In this case, the straddling pulse 210 may also be suppressed and the next full pulse 210 may be used instead. In FIG. 7, pulse 210 at P1 straddles the pixel readout period 206 and the blanking period 200. The pulse 210 at P1 is therefore suppressed and pulse 210 at P2 is used instead.

The disclosure relating to FIGS. 6 and 7 discussed when to allow pulses 210 and how to decide which pulse 210 to allow and be kept and used to create the frame scene. The decision process to determine when to allow pulses 210 and which pulse to allow, can be made more sophisticated by carefully choosing pulse duty cycles based on pulse frequency and blanking time to ensure consistent amounts of light reach the CMOS sensor 140. For instance, if the pulse train frequency is 150 Hz and the duty cycle is 10%, then that means the light is strobed for 0.6 ms every pulse. If the frequency changes to 500 Hz then careful selection of duty cycle based on the maximum and minimum number of pulses that could occur during a blanking period can ensure that the sensor is still pulsed for 0.6 ms. But the exposure time may be spread over multiple pulses.

Referring now to FIGS. 8-12, theoretically it may be difficult to significantly extend the blanking period 200 because it decreases the frame rate if same number of pixels is readout during the readout period 206. A lower frame rate will increase the number of superimposed images available during videostroboscopy, which might blur the resultant image. In turn, reducing the readout period 206 may be accomplished by reducing the image resolution, i.e., reading out fewer pixels, which may also have a negative impact on the final image.

Accordingly, if too many pulses are rejected, each superimposed image will not appear as crisp because of lower occurrence at the sensor frame rate. This may lead to low frequency flickering if the pulse rejection reaches a certain threshold.

The following discussion contemplates avoiding the situation where light strobes or pulses 210 are rejected during sensor readout 206 and therefore maintaining image crispness while maintaining resolution and frame rate. In one implementation, the rows that have integrated light originated from a given pulse and in which frame it will be readout may be tracked. Upon frame readout, digital gain will be applied to different row sections in the frame for normalization, and therefore compensate for any light deficit or light excess with respect to a computed reference level. Because of the slow motion used in videostroboscopy, there will be no motion artifact caused by this method.

Figure 8:
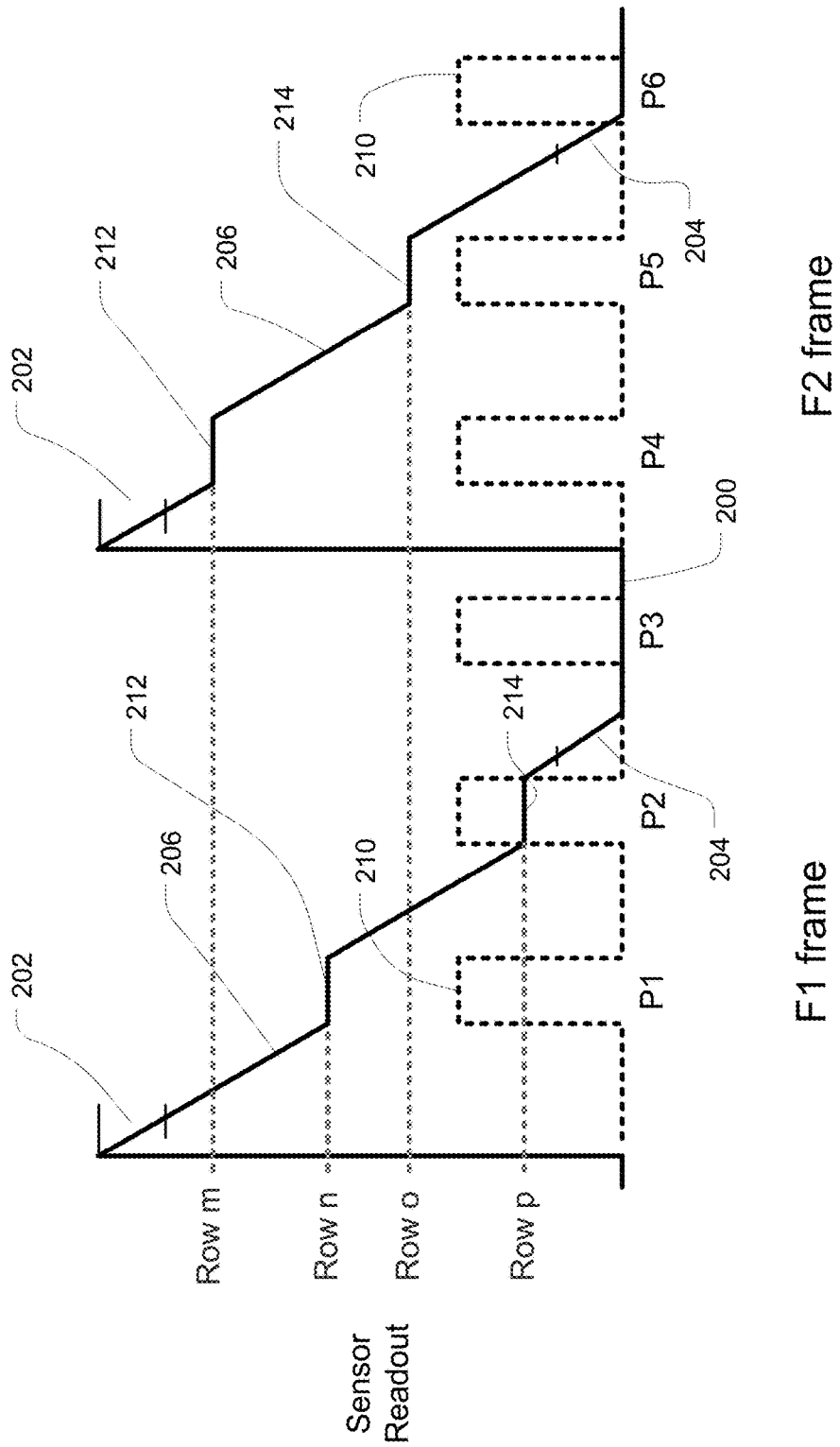
FIG. 8 illustrates an implementation where each readout frame has been suspended (two times as illustrated), where each suspension occurs at a time when a light pulse or strobe occurs.

Referring now to FIG. 8, the sensor readout 206 may be suspended when the light strobing starts. The sensor readout 206 may resume when the strobing finishes. Methods to suspend the sensor readout 206 may include, but are not limited to, freezing the sensor clock, freezing the sensor vertical decoder and/or the horizontal readout. It should be noted that there are multiple other methods to freeze the sensor readout and all such methods fall within the scope of this disclosure. FIG. 8 illustrates an example where each readout frame (F1 and F2) has been suspended twice (at 212 and 214), each time a light strobe or pulse 210 occurs.

Figure 9:
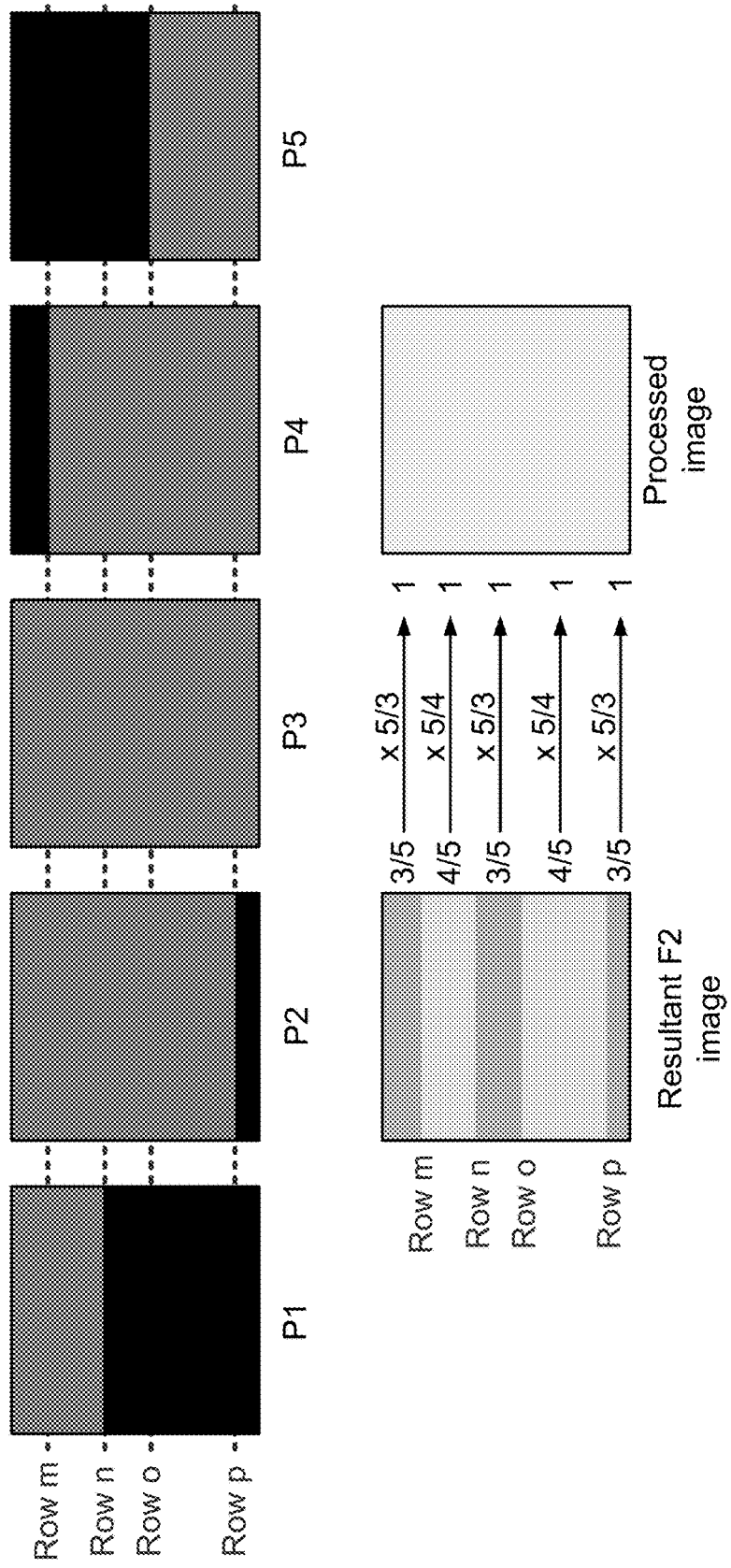
FIG. 9 illustrates a contribution made by each light pulse or strobe on the next sequential frame (illustrated as F2) and the resultant image composed by the five images relative to pulses P1 to P5 according to one implementation.

FIG. 9 illustrates the contribution of each light pulse (P1 to P5) on the F2 frame from FIG. 8. It can be seen that pulses 210 occurring during the F1 frame generate a lit top image and a black bottom image on the F2 frame. In contrast, pulses 210 occurring during the F2 frame generate a black top image and a lit bottom image on the F2 frame. As demonstrated earlier, a pulse 210 during the blanking period 200 provides a fully lit image on the next frame (see discussion in relation to FIG. 4). Because the readout 206 may be suspended during strobing, there is no gradient of light in the image relative to one pulse and a clear cut is seen at the physical row being readout right before the light pulse 210 starts. For example, the image from the pulse 210 at P1 sees the illumination relative to P1 light pulse from the top of the image until Row n. Thereafter, the image is black. The resultant image is the superimposition of all images relative to the relevant pulses 210 (P1 through P5 in the example).

FIG. 9 also illustrates the resultant F2 image composed by the five images relative to pulses 210 at P1 to P5. It can be seen that there are five distinct stripes that correspond to areas between Rows m, n, o and p, which have been exposed to different number of light strobes or pulses 210. For example, during the pulses P1 to P5 the stripe of rows between Row m and Row n has been exposed 4 times out of the 5 possible, whereas the stripe of rows between Row n and Row o has been exposed 3 times out of the 5 possible.

A processed image can then be substantially artifact-free by normalization using digital gain. In the FIG. 9 example, a digital gain of 5/3 will be applied to the stripe between the top of the pixel array and Row m, the stripe between Row n and Row o, and the stripe between Row p and the bottom of the pixel array. A digital gain of 5/4 will be applied to the stripe between Row m and Row n and the stripe between Row o and Row p.

Figure 10:
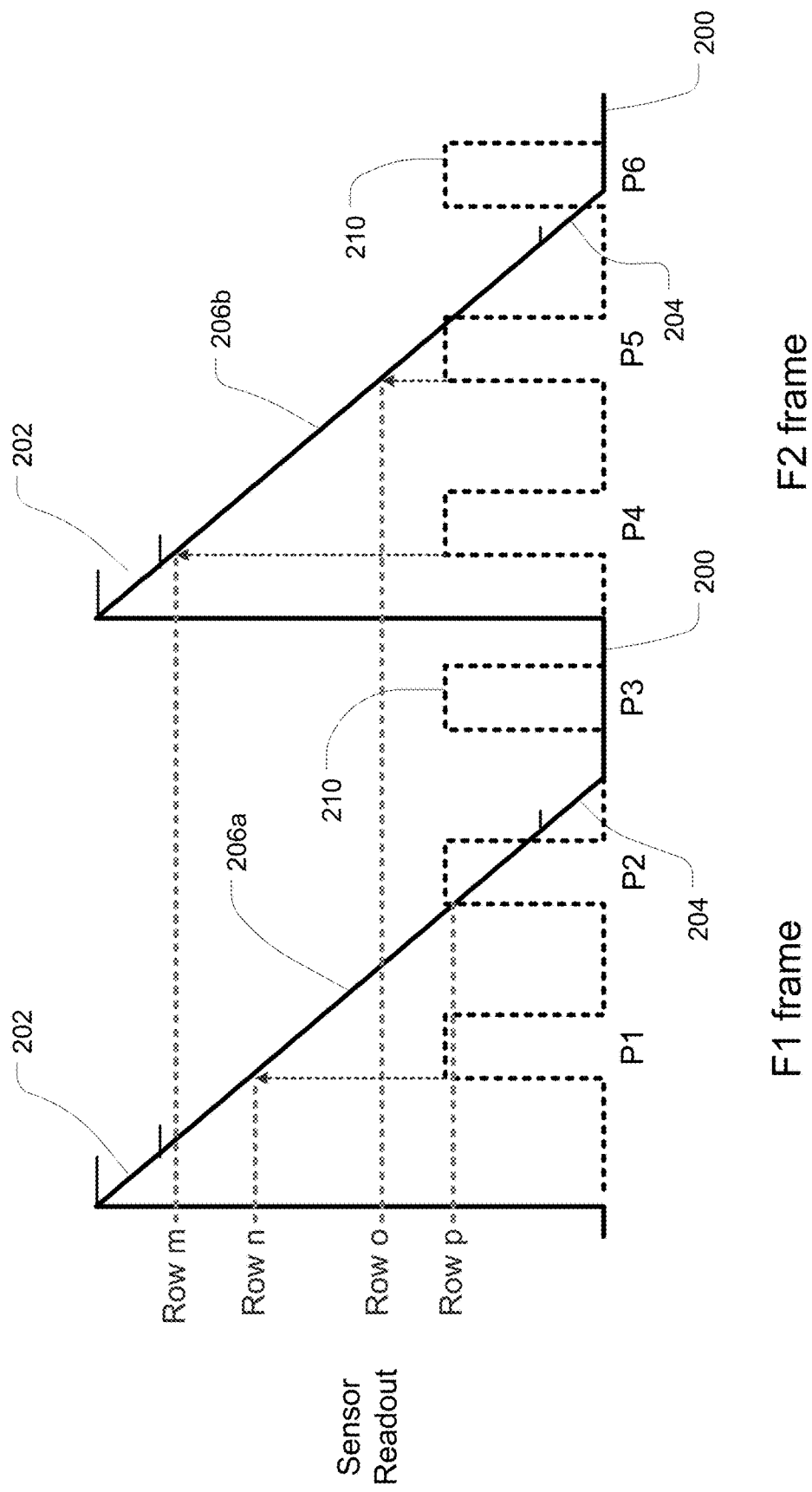
FIG. 10 illustrates a readout sequence with P1, P2, P4 and P5 pulses occurring during the readout and the P3 and P6 pulses occurring during the blanking time period 200 according to one implementation.
Figure 11:
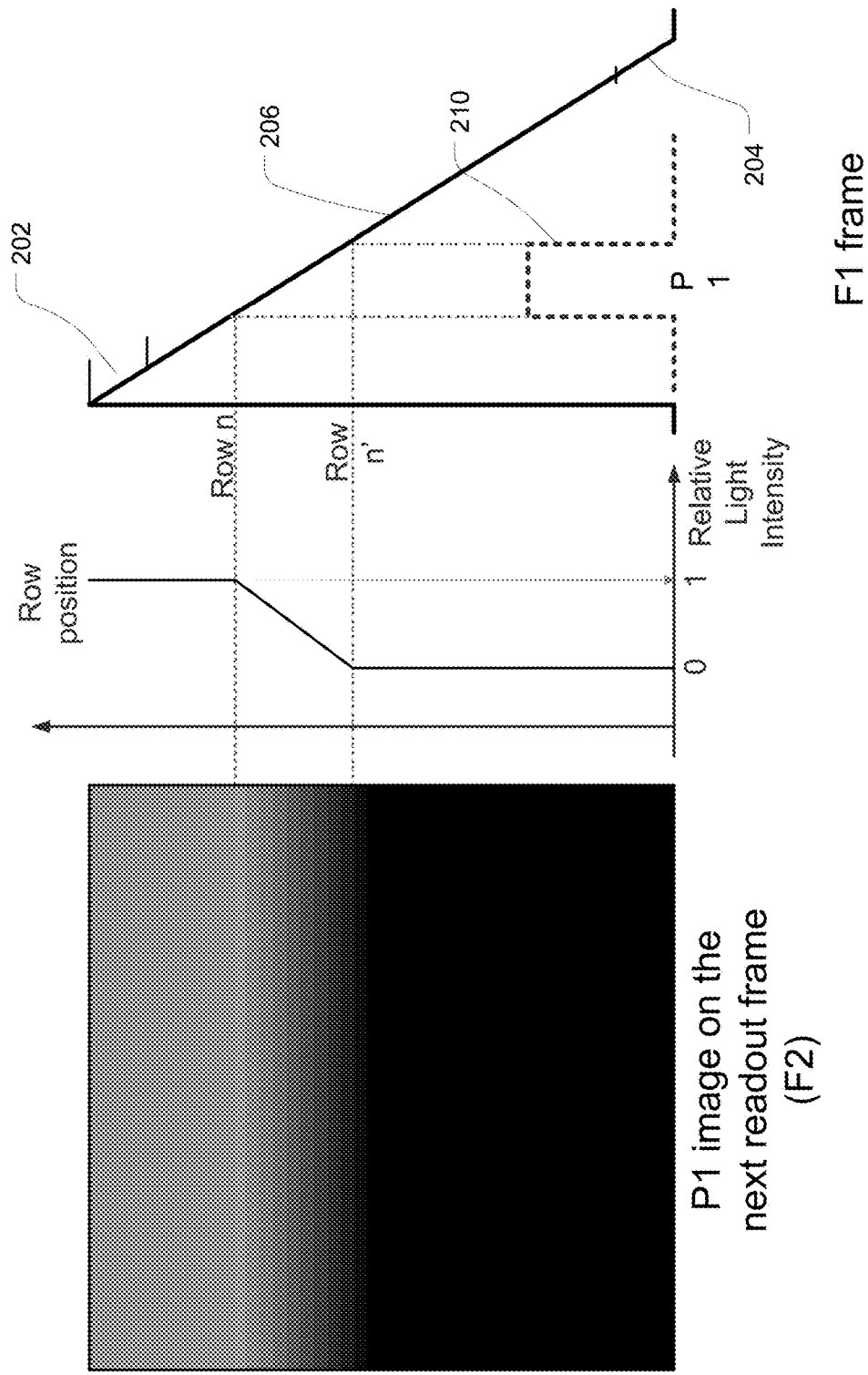
FIG. 11 illustrates an example of the resulting image related to a single pulse P1 that occurs during the sensor read out period according to one implementation.
Figure 12:
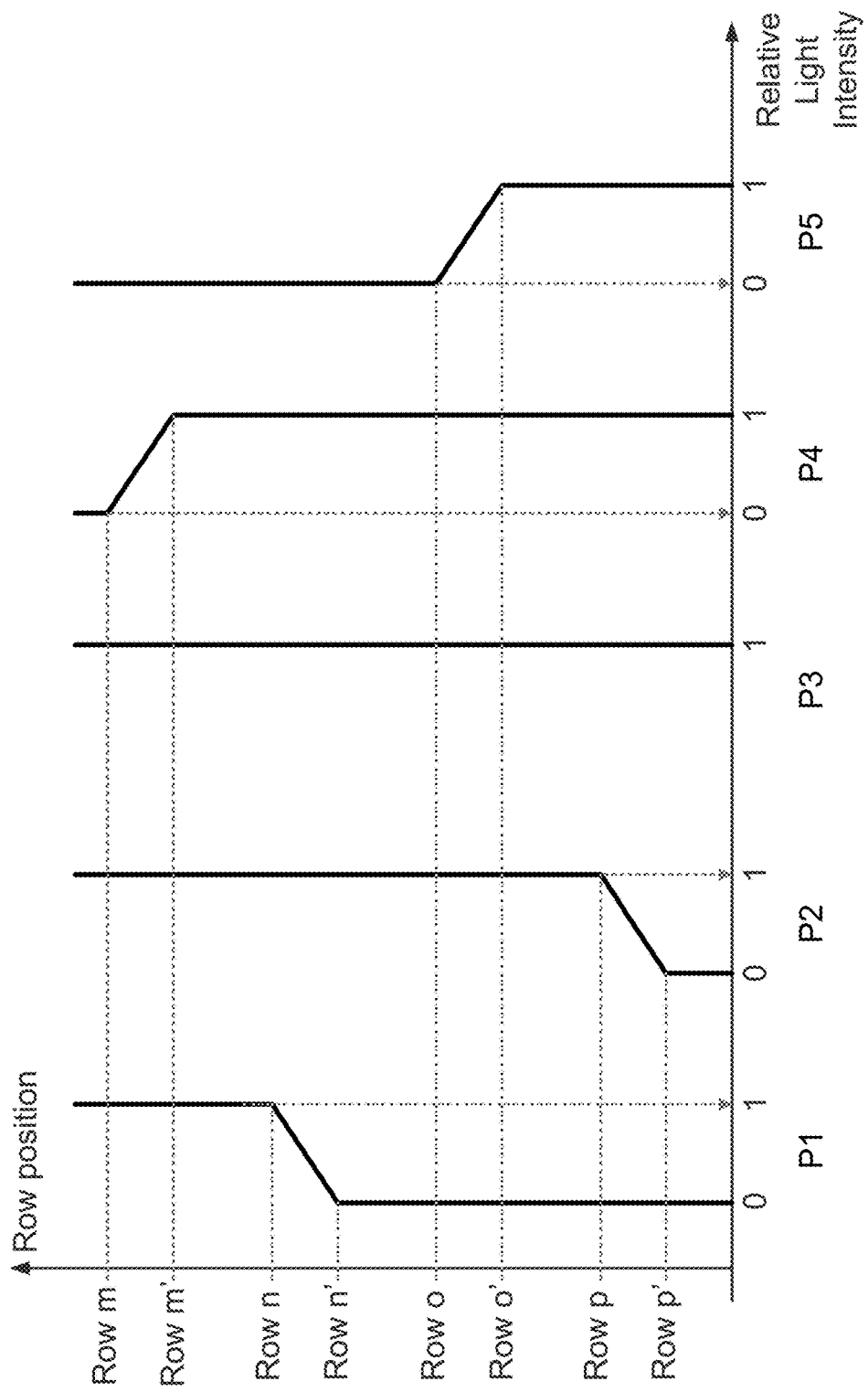
FIG. 12 illustrates a representation of row position versus relative light intensity for each of the strobes or pulses P1 to P5 of FIG. 10 according to one implementation.

Referring now to FIGS. 10-12, it may be difficult to suspend the sensor readout 206 as described in relation to FIGS. 8 and 9. The following discussion focuses more on the Image Signal Processing (ISP), while simplifying the hardware, especially the image sensor. The light pulses or strobes 210 that occur during the sensor readout 206 may be "recycled" without the need for suspending the readout process.

FIG. 10 illustrates an example of the readout sequence with pulses 210 at P1, P2, P4 and P5 occurring largely or entirely during the readout periods 206a and 206b, and the pulses 210 at P3 and P6 occurring during the blanking periods 200. Because of the superimposition of images related to a single pulse 210, the study of one of these images is enough to explain the entire method. For example, the focus of the discussion may be placed on pulse P1.

FIG. 11 illustrates an example of the resulting image related to a single pulse 210 (P1 in this case) that occurs during sensor readout 206. Note that the readout remains uninterrupted. The P1 image shown in this example is readout on the next readout frame (F2). The readout of the top row (for example Row 0) until Row n will happen prior to the P1 strobe 210. As such, the entire light energy generated by the P1 pulse 210 will be held on these rows until the next readout (F2). When the P1 strobe 210 and the readout occur concurrently, the part of the light that is generated between the start of the strobe and the F1 readout of a given row gets readout on the F1 frame. The light of the remaining part of the light pulse (after the F1 readout of the given row) will be seen during the F2 readout of this given row. The rows that are concerned with the splitting of the light are between Row n and Row n'.

By way of example, if it is supposed that the 5th row after the start of the P1 pulse (i.e., Row n+5) is being readout (F1 frame), then an equivalent of 5 line times of the light pulse has been integrated and read out during the F1 readout. The remaining part of the pulse 210, which is the pulse width minus 5 line times, will be readout on the F2 frame. Because the F1 frame readout occurs after the P1 strobe, the light information generated on the pixels from Row n' to the end of the pixel array will be readout during the F1 frame readout and nothing relative to this P1 pulse 210 will be present at the time of the F2 frame readout, leading to a black area in the F2 frame.

Because the line time of the sensor (Tline) and the pulse width (Tpulse) are precisely controlled and timed, the light deficit on the rows between Row n and Row n' at the frame F2 readout can be calculated as a function of line position. First, one needs to calculate the number of rolling rows (Δ) during strobe width:

In the FIG. 11 example, n'=n+Δ

$$\Delta = \frac{Tpulse}{Tline}$$

For pulses 210 occurring during the F1 frame (e.g., pulse P1), the relative illumination (I) of a row x collected in the F2 frame can be expressed by:

$$x < n \rightarrow I = 1$$
$$n \leq x \leq n + \Delta \rightarrow I = 1 - \frac{x - n}{\Delta}$$
$$x > n + \Delta \rightarrow I = 0$$

This is illustrated in the graph (row position) versus (relative light intensity) in FIG. 11. With very similar reasoning, the expression of the relative illumination (I) of a row x collected in the F2 frame for pulses occurring during F2 frame (e.g. P5 in FIG. 10) is:

$$x < o \rightarrow I = 0$$
$$o \leq x \leq o + \Delta \rightarrow I = \frac{x - o}{\Delta}$$
$$x > o + \Delta \rightarrow I = 1$$

FIG. 12 illustrates a representation of (row position) versus (relative light intensity) for each of the strobes 210 at P1 to P5 from the example in FIG. 10. As explained above, P1 and P2 are pulses 210 that are occurring during the frame F1 readout 206a and have the full light illumination for the top rows and have black bottom rows. In turn, pulses 210 at P4 and P5 that occur during the F2 readout 206b have black top rows and fully illuminated bottom rows. In all cases, a linear transition happens when the readout 206a and readout 206b are concurrent. The image from P3 has full illumination because P3 is positioned during the sensor blanking time 200.

As explained earlier in relation to FIGS. 8 and 9, a resultant image can be obtained by superimposing all images relative to the relevant light pulses. The ISP can keep track of the light deficit for each row (using the diagram of FIG. 12 and above mathematic expressions) and then applying a row-wise digital gain to normalize the resultant image into an artifact-free image.

In one implementation, the intensity of the light source can be controlled during each strobe (strobe height) in order to maintain a desired constant output level at any strobing frequency.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Figure 13A:
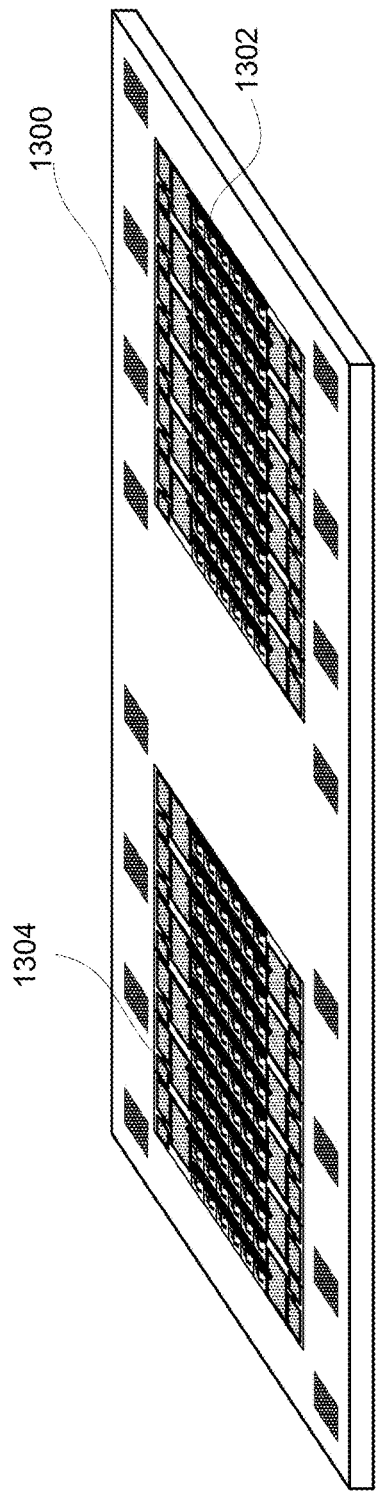
FIGS. 13A and 13B illustrate a perspective view and a side view, respectively, of an implementation of a monolithic sensor having a plurality of pixel arrays for producing a three dimensional image in accordance with the teachings and principles of the disclosure.
Figure 13B:
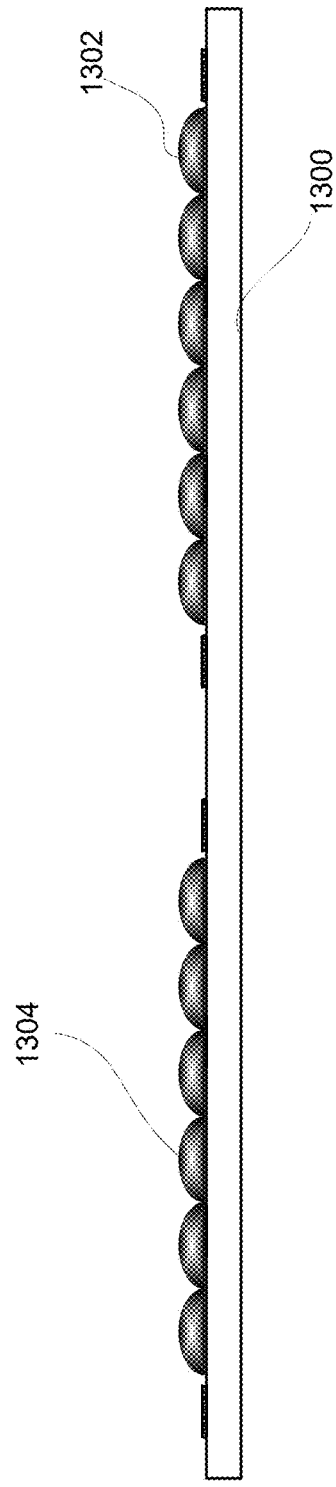

Referring now to FIGS. 13A and 13B, the figures illustrate a perspective view and a side view, respectively, of an implementation of a monolithic sensor 1300 having a plurality of pixel arrays for producing a three dimensional image in accordance with the teachings and principles of the disclosure. Such an implementation may be desirable for three dimensional image capture, wherein the two pixel arrays 1302 and 1304 may be offset during use. In another implementation, a first pixel array 1302 and a second pixel array 1304 may be dedicated to receiving a predetermined range of wave lengths of electromagnetic radiation, wherein the first pixel array 1302 is dedicated to a different range of wave length electromagnetic radiation than the second pixel array 1304.

Figure 14A:
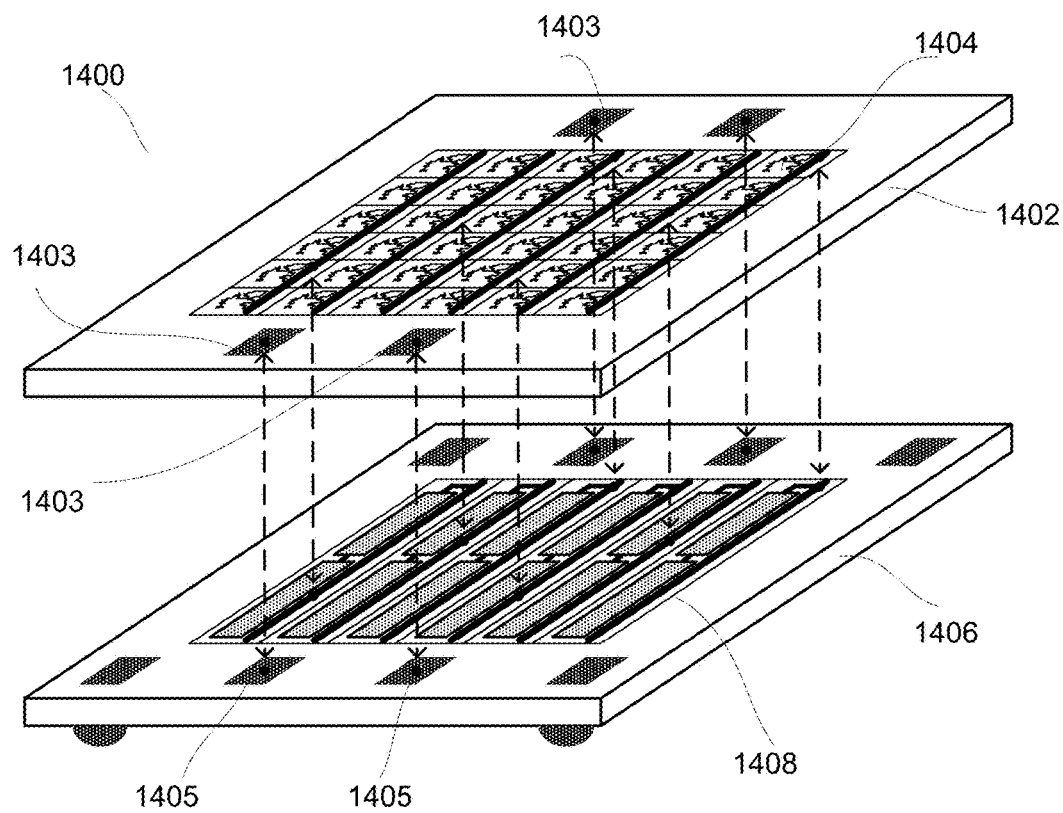
FIGS. 14A and 14B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 14B:
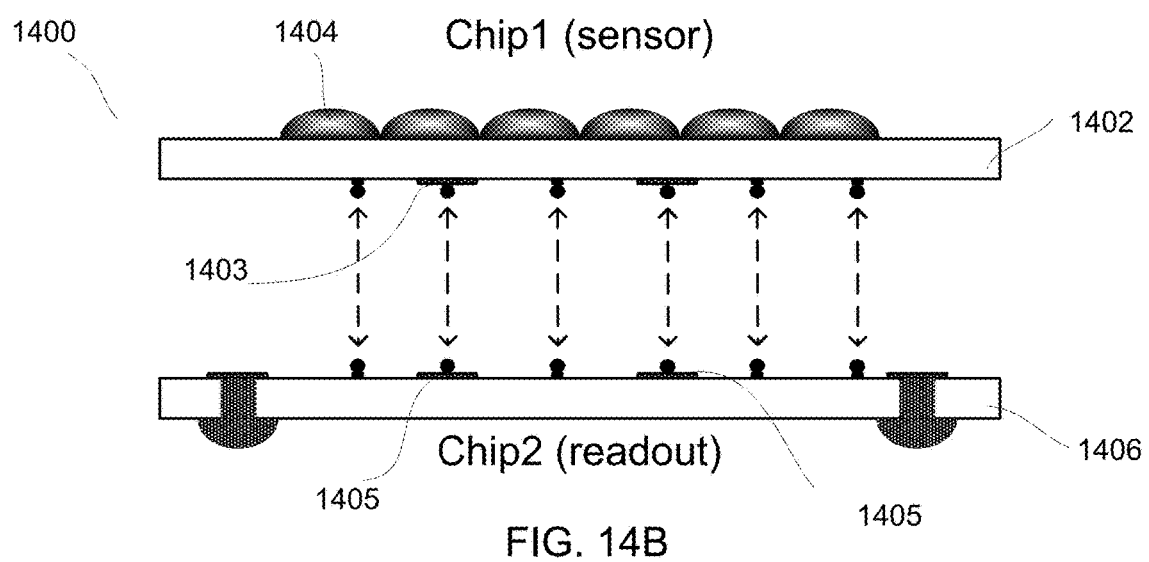

FIGS. 14A and 14B illustrate a perspective view and a side view, respectively, of an implementation of an imaging sensor 1400 built on a plurality of substrates. As illustrated, a plurality of pixel columns 1404 forming the pixel array are located on the first substrate 1402 and a plurality of circuit columns 1408 are located on a second substrate 1406. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 1402 of the two substrates/chips may be processed using an image CMOS process. The first substrate/chip 1402 may be comprised either of a pixel array exclusively or a pixel array surrounded by limited circuitry. The second or subsequent substrate/chip 1406 may be processed using any process, and does not have to be from an image CMOS process. The second substrate/chip 1406 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 1402 may be stacked with the second or subsequent substrate/chip 1406 using any three-dimensional technique. The second substrate/chip 1406 may support most, or a majority, of the circuitry that would have otherwise been implemented in the first image CMOS chip 1402 (if implemented on a monolithic substrate/chip) as peripheral circuits and therefore have increased the overall system area while keeping the pixel array size constant and optimized to the fullest extent possible. The electrical connection between the two substrates/chips may be done through interconnects 1403 and 1405, which may be wirebonds, bump and/or TSV (Through Silicon Via).

Figure 15A:
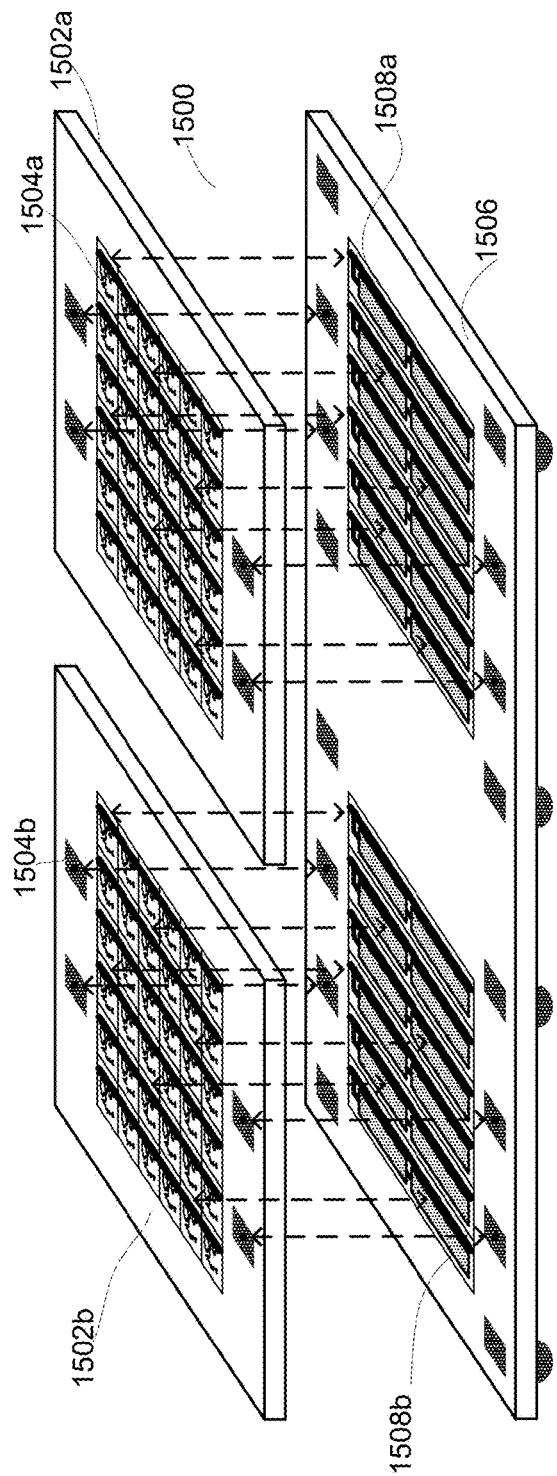
FIGS. 15A and 15B illustrate a perspective view and a side view, respectively, of an implementation of an imaging sensor having a plurality of pixel arrays for producing a three dimensional image, wherein the plurality of pixel arrays and the image sensor are built on a plurality of substrates.
Figure 15B:
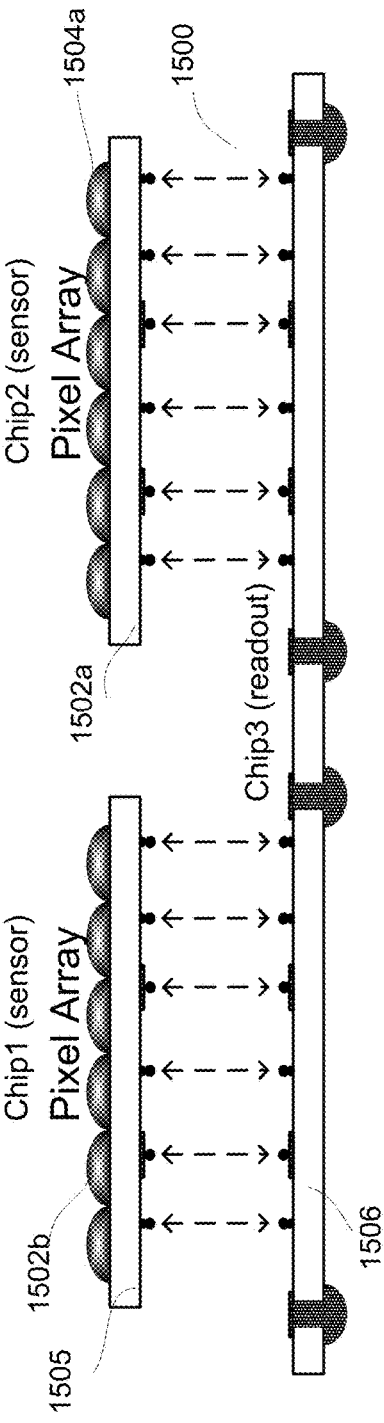

FIGS. 15A and 15B illustrate a perspective view and a side view, respectively, of an implementation of an imaging sensor 1500 having a plurality of pixel arrays for producing a three dimensional image. The three dimensional image sensor may be built on a plurality of substrates and may comprise the plurality of pixel arrays and other associated circuitry, wherein a plurality of pixel columns 1504a forming the first pixel array and a plurality of pixel columns 1504b forming a second pixel array are located on respective substrates 1502a and 1502b, respectively, and a plurality of circuit columns 1508a and 1508b are located on a separate substrate 1506. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method for providing an image comprising:
continuously determining a frequency of a patient's vocal cords during a videostroboscopy procedure;
strobing light from a light source at a strobing frequency that substantially matches the patient's vocal cord frequency;
receiving a plurality of pulses of light from the light source as strobing input by a CMOS sensor during a pixel readout portion of a readout sequence and during a blanking portion of a readout sequence; and
reading out information obtained from the CMOS sensor to a processor, wherein at least one of the plurality of pulses of light from the light source is suppressed during one or both of the pixel readout portion of the read out sequence and the blanking portion of the readout sequence such that an aggregate amount of illumination which is the sum of the amplitude and the duration of all nonsuppressed pulses for a first blanking period is equal to the aggregate amount of illumination level of in a successive blanking period.

2. The method of claim 1, wherein the method further comprises eliminating artifacts by disabling the strobing during a CMOS sensor readout period.

3. The method of claim 1, wherein the method further comprises suppressing the plurality of pulses of light that straddle the pixel readout portion and the first blanking period.

4. The method of claim 1, wherein the method further comprises suspending each sensor readout frame at least once creating a suspension period, and strobing light during the suspension period.

5. The method of claim 4, wherein the method further comprises suspending the sensor readout frame a plurality of times per frame, and strobing light during each suspension period.

6. The method of claim 1, wherein the method further comprises superimposing all images obtained during a readout sequence in relation to corresponding light pulses.

7. The method of claim 1, wherein the method further comprises applying a digital gain to a subset of rows in a frame in relation to a corresponding light pulse position.

8. The method of claim 1, wherein the method further comprises applying a plurality of digital gains to a plurality of subsets of rows in a frame in relation to corresponding light pulse positions.

9. The method of claim 1, wherein the method further comprises applying a dedicated digital gain to all rows in a frame in relation to corresponding light pulse positions.

10. The method of claim 1, wherein the method further comprises superimposing sensor readout frames corresponding to the plurality of pulses of light to obtain a resultant image.

11. The method of claim 10, wherein the method further comprises tracking a light deficiency for each row of the CMOS sensor in each superimposed sensor readout frame.

12. The method of claim 11, wherein the method further comprises applying a digital gain to normalize the resultant image into an artifact-free image.

13. A method for providing an image comprising:
- determining a frequency of a patient's vocal cords during a videostroboscopy procedure;
- strobing light from a light source at a strobing frequency that substantially matches the patient's vocal cord frequency;
- receiving a plurality of pulses of light from the light source as strobing input by a CMOS sensor during a pixel readout portion of a readout sequence and during a blanking portion of a readout sequence;
- reading out information obtained from the CMOS sensor to a processor, wherein at least one of the plurality of pulses in the light from the light source is suppressed during one or both of the pixel readout portion of the readout sequence and the blanking portion of the readout sequence such that an aggregate amount of illumination which is the sum of the amplitude and the duration of all nonsuppressed pulses for a first blanking period is equal to the aggregate amount of illumination level of in a successive blanking period;
- creating a sensor readout frame for each readout sequence of the CMOS sensor; and
- wherein creating the sensor readout frame comprises superimposing a plurality of pulses of light to obtain a resultant image.

14. A method for providing an image comprising:
- determining a frequency of a patient's vocal cords during a videostroboscopy procedure;
- strobing light from a light source at a frequency that substantially matches the patient's vocal cord frequency;
- receiving a plurality of pulses of light from the light source as strobing input by a CMOS sensor during a pixel readout portion of a readout sequence and during a blanking portion of a readout sequence;
- reading out information obtained from the CMOS sensor to a processor, wherein at least one of the plurality of pulses of light from the light source is suppressed during one or both of the pixel readout portion of the read out sequence and the blanking portion of the readout sequence such that an aggregate amount of illumination which is the sum of the amplitude and the duration of all nonsuppressed pulses for a first blanking period is equal to the aggregate amount of illumination level of in a successive blanking period;
- creating a sensor readout frame for each readout sequence of the CMOS sensor, wherein a light pulse from the light source occurs during a first readout frame of the CMOS sensor;
- superimposing sensor readout frames comprising the first readout frame and a subsequent readout frame to obtain a resultant image;
- tracking a light deficiency for each row of the CMOS sensor in each superimposed sensor readout frame; and
- applying a digital gain to normalize the resultant image into an artifact-free image.

* * * * *